«12» United States Patent
Brooks

«10» Patent No.: US 6,770,793 B2
«45» Date of Patent: Aug. 3, 2004

«54» DISPOSABLE ABSORBENT WOUND DRESSING WITH SKIN HEALTH TREATMENT ADDITIVES

«75» Inventor: JoAnn Brooks, Arlington, TX (US)

«73» Assignee: Kimberly-Clark Worldwide, Inc., Neenah, WI (US)

«*» Notice: Subject to any disclaimer, the term of this patent is extended or adjusted under 35 U.S.C. 154(b) by 0 days.

«21» Appl. No.: 10/215,551

«22» Filed: Aug. 8, 2002

«65» Prior Publication Data

US 2004/0030283 A1 Feb. 12, 2004

«51» Int. Cl.⁷ ............................ A61F 13/00; A61F 13/02
«52» U.S. Cl. ........................................ 602/48; 604/307
«58» Field of Search ................................. 424/445–449, 424/402; 602/41–62; 604/305–308; 428/311.71

«56» References Cited

U.S. PATENT DOCUMENTS

| | | | |
|---|---|---|---|
| 4,838,253 A | * 6/1989 | Brassington et al. | ......... 602/48 |
| 5,147,338 A | * 9/1992 | Lang et al. | ................. 604/304 |
| 5,952,088 A | 9/1999 | Tsai et al. | |
| 6,107,537 A | * 8/2000 | Elder et al. | ................. 604/364 |
| 6,197,237 B1 | 3/2001 | Tsai et al. | |
| 6,306,782 B1 | 10/2001 | Tsai et al. | |
| 6,475,197 B1 | * 11/2002 | Krzysik et al. | ............. 604/304 |

* cited by examiner

*Primary Examiner*—John J. Calvert
*Assistant Examiner*—Linh Truong
«74» *Attorney, Agent, or Firm*—Brinks Hofer Gilson & Lione

«57» ABSTRACT

The present invention relates to disposable absorbent wound dressings comprising skin health treatment additives for the treatment and prevention of Stage I–IV partial and full thickness pressure wounds. The disposable dressings conform to the anatomical shape of the body of a human and are capable of absorbing large quantities of wound drainage or exudates. Such disposable dressings are low-adherent and facilitate painless removal without disturbing a healing tissue bed. Such disposable wound dressings of the present invention are especially advantageous for the treatment of Stage I–IV pressure ulcers located in the sacral/coccyx area of the spine.

14 Claims, 1 Drawing Sheet

DISPOSABLE ABSORBENT WOUND DRESSING WITH SKIN HEALTH TREATMENT ADDITIVES

FIELD OF THE INVENTION

The invention relates to wound dressings comprising skin health additives. Skin health additives are applied to the layer of the wound dressing that will come into contact with the skin of a wearer. In particular, these disposable absorbent wound dressings are useful for protecting the skin and preventing and healing pressure ulcers, especially in the sacral-coccyx region of a human.

BACKGROUND OF THE INVENTION

Of particular concern to medical practitioners is the formation of pressure ulcers in incapacitated individuals, such as bed-ridden patients, mentally challenged persons who are unable to perform personal hygiene, individuals who are incontinent, or hospital patients recovering from spinal cord injuries, surgery, or debilitating strokes. These individuals may be subject to the formation of pressure ulcers due to prolonged pressure on parts of the body from long periods of remaining in a stationary position, the exposure of the skin to feces and urine, or a combination of circumstances. Pressure ulcers generally occur in the sacral-coccyx area, however, these ulcers can also occur on hips, feet, and the skin covering elbows and shoulder blades. Pressure ulcers are a significant concern for health care providers because these chronic wounds cause increased healthcare provider costs. In the U.S. alone, the prevalence of chronic wounds has been estimated to occur in nearly 6 million patients. The cost involved in treating these wounds averages $3,000 per patient, totaling over $13 billion per year for healthcare costs in the United States.

Wound dressings are often used to treat pressure ulcers. Wound dressings typically consist of fibrous material arranged in layers with a fluid impervious layer or back sheet to prevent exudates from seeping through the dressing. Wound dressings are often made of cotton gauze with a polymer top sheet. Medicaments are often manually applied to the dressings before positioning on the wound. The dressings are generally flat sheets and do not conform well to the anatomy of individuals who have pressure ulcers, especially in the sacral-coccyx area, because these individuals are often thin and lacking in muscle mass and tissue elasticity. Furthermore the dressings must be changed frequently and this exacerbates the irritation to the skin.

Wound dressings can be subjected to one or more liquid insults, such as of water, urine, feces, or blood, during use. As such, the outer cover backsheet materials are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product. However, the lack of air flow in wound dressings can inhibit healing due to the growth of anerobic bacteria. Furthermore, these dressings do not cushion wounds or conform to certain areas of the body, such as the sacral-coccyx area.

What is needed in the art is a wound dressing comprising an anhydrous silicone based skin health additive pre-applied directly to the dressing which will facilitate the ease of removal without disturbing the healing tissue. What is also needed in the art is a wound dressing that will conform to the anatomy of the wearer, especially in the sacral and coccyx area to cushion and protect the wearer. Another useful feature is the inclusion of superabsorbent materials capable of absorbing up to 20 times their weight in wound drainage or exudate fluids. These and other needs are provided by the present invention.

SUMMARY OF THE INVENTION

Figure 1:
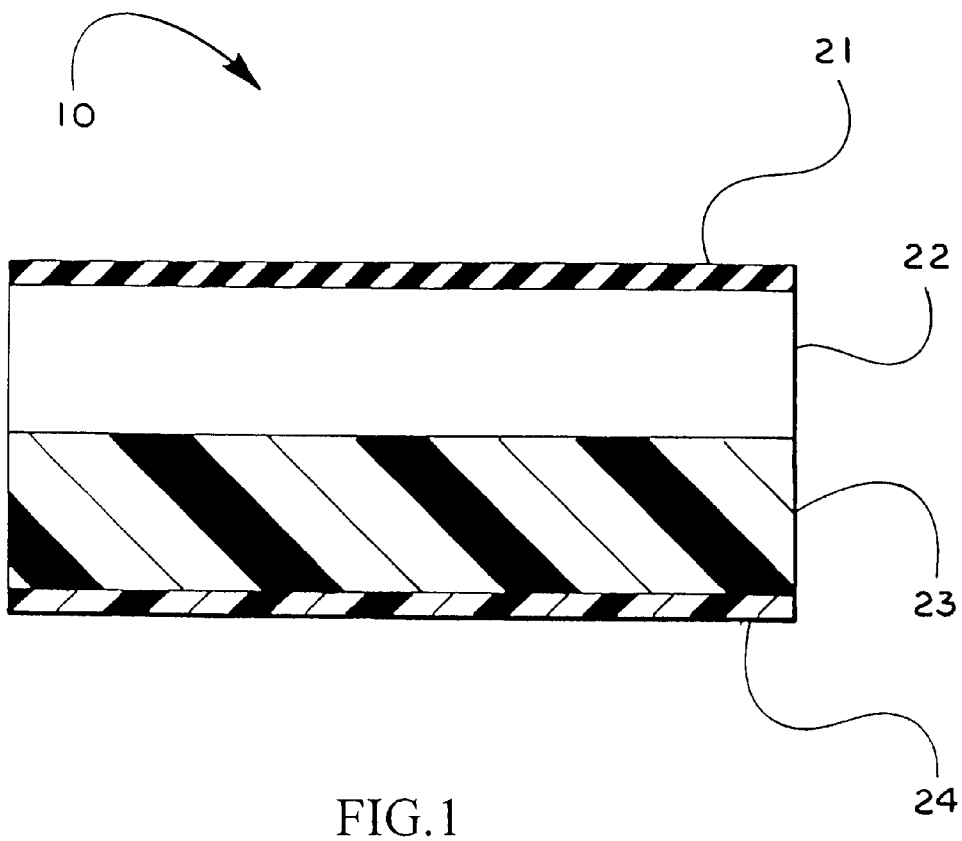
FIG. 1 is an aspect of the wound dressing of the present invention.

The invention relates to disposable wound dressings containing silicone based skin health treatment additives. More particularly, the invention relates to disposable wound dressings comprising a skin contact layer of apertured non-woven fabric treated with a silicone based skin health treatment additive, a liquid permeable top-sheet with a fluffed cellulose and superabsorbent matrix, a flexible polyurethane foam cushion layer, and a liquid impermeable film comprising a vapor permeable back-sheet.

DETAILED DESCRIPTION OF THE INVENTION

As depicted in the Figure, the disposable wound dressings (10) of the present invention comprise a top-sheet (22) of fluffed cellulose and superabsorbent polymers in a fiberized matrix and a polyurethane biocompatible foam layer (23) capable of absorbing exudates unable to be contained by the top sheet matrix (22). The biocompatible foam layer (23) also provides cushion to sacral coccyx area of the human spine. The invention further comprises a liquid non-permeable layer (24) which is comprised of a vapor permeable film on the back surface of the dressing. A silicone based skin health treatment additive can be applied consistently and uniformly to a layer of non-woven apertured fabric, the skin contact layer (21), which covers the outer surface of the top-sheet (22) in an area that will come into direct contact with the sacral/coccyx area of the wearer. Advantageously the biocompatible foam layer (23) comprises a material that conforms to the anatomy of the wearer and forms a cushion to protect from further tissue load pressure on the skin. Dressings of the present invention are especially advantageous for the treatment of Stage I–IV pressure ulcers located in the sacral-coccyx area of the spine.

The skin health treatment additive comprises at least one neutral carrier compound for impregnating the surface of the dressing. In one aspect of the invention, the skin health treatment additive can include an enzyme blocking compound and/or a skin replenishing compound, and a barrier compound. Advantageously, the skin health treatment additive can further comprise anti-microbial compounds, vitamins, antibiotics, genetically engineered tissue regeneration drugs, or combinations thereof.

Two types of approaches are indicated for the management of pressure ulcers in the sacral-coccyx area of the spine which is the area most vulnerable to pressure related skin breakdown. In a first aspect of the dressings of the present invention for treating ulcers in the sacral-coccyx, pressure point cushioning and protection are provided with minimal absorptive properties. The skin contact layer can comprise, for example, an apertured nonwoven fabric which can be impregnated with a neutral triglyceride wax such as Softisan 378 containing skin health additives. Such skin health additives can include, but are not limited to, vitamins, oil soluble vitamin C, zinc oxide and Disodium EDTA. The zinc oxide and the EDTA are typically dispersed in a heated anhydrous vehicle.

Additional aspects of the dressing can include, but are not limited to, a non-woven layer of breathable materials to lend integrity to the polyurethane foam while allowing air circulation to the skin. Additionally, a continuous adhesive component can maintain the dressing over the sacral-coccyx area of the spine. Alternatively, the dressing can be secured with silk or paper tape in a picture frame style of application. The shape of the dressing can be any geometric shape that effectively covers the sacral-coccyx area of the spine. A preferred shape is a rectangle with elongation sufficient to provide coverage of the area.

The foregoing aspect of the invention is lubricating to the pressure prone areas of the spine and comprises revitalizing vitamins, natural triglyceride waxes and enzyme inhibition additives to minimize the development of malodorous compounds emanating from bacteria in wound beds. In another aspect of the invention, a wound dressing is indicated for the patient with Stages II, III or IV pressure ulcers. Stage II ulcers include partial thickness skin loss involving epidermis, dermis, or both. Stage III involves full thickness skin loss involving damage or necrosis of subcutaneous tissue that may extend down to, but not through, the underlying fascia. Stage IV ulcers show full thickness skin loss with extensive destruction, tissue necrosis, or damage to muscle, bone, or supporting structures.

Various aspects of the invention can include, but are not limited to, a skin contact porous permeable non-woven layer impregnated with the skin treatment additives. A second layer adjacent to the outer layer can be a super absorbent layer comprising super absorbent particles suspended in a fluffed cellulose matrix which is capable of absorbing blood and exudates or drainage from the wound bed. Advantageously, an apertured non-woven netting skin contact layer can be secured such that the super absorbent particles can be tightly contained as a non-migrating matrix. Such super absorbent particles can comprise a size ranging from about 50 to about 600 microns. Most preferably the size comprises from about 300–500 microns.

Dressings of the present invention can comprise an additional non-permeable polymer matrix layer to prevent urine or feces from saturating the dressing from the outside. Such layers can comprise a polymer including, but not limited to, polypropylene. The non-permeable layer is advantageously the outer layer or the layer furthermost from the wound location. The outer layer is intended to contain potentially infectious exudates from the wound bed. This invention is especially advantageous in the home care environment where caregivers would not have access to expensive equipment to manage tissue load pressure such as air fluidized beds.

Additionally, skin health benefit additives can comprise topical antimicrobial compounds or topical antibiotics. Topical antimicrobials can include, but are not limited to, 1% silver sulfadiazine and 1% Provodone-iodine. Topical antibiotics can include, but are not limited to, 0.8% metronidazole.

The skin health treatment additives of the present invention may contain therapeutically acceptable auxiliary substances as required to approximate physiological conditions and as necessary to prepare the skin health treatment additive for convenient administration. Actual methods for preparing pharmaceutically administrable compounds will be known or apparent to those skilled in the art and are described in detail in, for example, Remington's Pharmaceutical Science.

The skin health treatment additives can be pre-applied uniformly and consistently to the surface of a dressing using any method known in the art, and can be subsequently packaged to be used at a time that is convenient for the individual or a caretaker. For purposes of the invention, the term pre-applied refers to any manufacturing process that would apply the agents to the surface of the dressing, although the agent could also be applied manually prior to use.

Skin health additives for the present invention can include, but are not limited to, those components listed in the following table:

EXAMPLE 1

| Ingredient | % of Total Weight |
| --- | --- |
| Caprylic/Capric/Stearic Triglyceride (Softisan 378) | QS to 100% |
| Tetrahexyldecyl Ascorbate (Barnet Products BVOSC) | 1.5–2.5% |
| Stearoxytrimethylsilane (and) Stearly Alcohol (Dow Corning 580 Wax) | 1.5–2.0% |
| Shea Butter (Lipo Chemicals) | 1.5–2.5% |

The coating of the skin health treatment additive can be applied to wound dressings by suitable methods apparent in the art including, but not limited to, spray application, slot coating, bead coating, rotary silk screening processes, evaporative coating, extrusion, or combinations thereof. The skin health treatment additive can be applied in a geometric pattern or a random pattern to the surface of the dressing that will contact the skin of the wearer. Preferably, the skin health treatment additive can be applied in a discreet area positioned for contact with the skin of an individual. A uniform and consistent coating of the skin health treatment additive provides maximum protection to the skin. Advantageously, the application of additive is in the geometric form of a circle, an oval, a square, a rectangle, a triangle, or combinations, thereof.

Advantageously, dressings of the present invention can be in the form of a flat sheet-like pad in various sizes and configurations. Alternatively, dressings can be in the form of strips, or can be wound into an ovoid, rectangular or cylindrical form. The methods of making such dressings are known in the art. Preferably, the dressing comprises a size of about twelve inches by about ten inches. Most preferably the dressing comprises a size of about five inches by about seven inches. Most preferably the dressing comprises a size that covers and conforms to a location of a pressure ulcer on the body of a human, especially in the sacral-coccyx or tailbone region.

Wound dressings of the present invention comprise a super absorbent polymer layer comprising super absorbent particles in a size range of from about 300 to about 500 microns in diameter of partially neutralized acrylic acid polymers to absorb exudates and manage odor emanation from infected wound beds. This layer can be prepared using fiberization with fluffed cellulose to provide additional cushioning to the sacral/coccyx area of the spine.

Wound dressings of the present invention comprise a skin health additive comprising lipid rich triglyceride wax to soften necrotic tissue and eschar formation to aid debridement and promote healing, and can comprise an oil soluble vitamin C to stimulate collagen synthesis. Wound dressings of the present invention further comprise a silicone wax to provide low adherence and pain free removal of the soiled dressing.

Wound dressings of the present invention comprise a wound contact layer of apertured non-woven net to allow rapid fluid intake and removal of exudates into the superabsorbent polymer layer.

Wound dressings of the present invention comprise a hydrophilic layer of polyurethane foam to further absorb exudates and cushion the sacral/coccyx area of the spine.

Such wound dressings of the present invention can be supplied on a bulk roll or in precut shapes of ovals, rounds, or squares. The present invention can be used as a vehicle for topical antibiotics, antimicrobials, and genetically engineered tissue recovery medicaments. Advantageously, wound dressings of the present invention can further comprise a backing of vapour-permeable polyethylene to promote air circulation to the wound bed.

Wound dressings of the present invention comprise materials which are free of microbes, lint, and trace chemical contaminants which may impede healing and can be supplied with a skin adhesive layer or used in combination with silk or paper tape to allow tight adherence and protection from other body fluid irritants and waste that may be in the area of the wound bed.

Wound dressings of the present invention comprise a skin/wound contact layer comprised of a thin apertured non-woven netting or hydroknit to which the lipid/vitamin/silicone low adherent treatment has been saturated/permeated or coated thereupon. The holes in the surface netting can enhance the exudate fluid acquisition into an air laid layer with the super absorbent polymer/fluffed cellulose matrix. The top layer can also be used to deliver medicaments such as topical antimicrobials, antibiotics, biochemical healing cofactors such as zinc, oil soluble stable vitamin C derivatives, enzymatic debriding chemicals, alginate powders, and genetically engineered tissue recovery drugs.

Wound dressings of the present invention comprise a highly absorbent air laid layer positioned just below the treated aperture or hydronit netting comprising the super absorbent polymers blown into the fluffed cellulose in a matrix composed of polymer particles having an optimal range of 300–500 microns across. The most preferable fluffed cellulose is derived from wood pulp process technology with patents held globally by Kimberly Clark. Superabsorbent materials are available from Dow Chemical, Midland, Mich.

Wound dressings of the present invention comprise a hydrophilic polyurethane foam layer comprising a polymeric foam with the appearance of a sponge which provides a conforming fit that is useful for providing cushion to the sacral/coccyx area of the spine. Such layer can be formed into extruded sheets or into a variety of shapes including oval, round or square.

Wound dressings of the present invention can comprise a vapor permeable back layer composed of a thin breathable layer of polyethylene which allows air circulation but is intended to contain potentially infectious microbes often found in exudates or drainage from a wound bed.

In addition to the wound dressing itself, typically the packaging in which the dressing is distributed is also made from a water-barrier, specifically water-resistant, material. Water-resistivity is necessary to prevent the degradation of the packaging from environmental conditions and to protect the wound dressing prior to use. The wound dressing can be sterilized by any method known in the art that is suitable for the dressing and the skin health treatment additive.

Although the particular aspects of the invention have been described, it would be obvious to one skilled in the art that various other modifications can be made without departing from the spirit and scope of the invention. It is therefore intended that all such changes and modifications are within the scope of the appended claims.

What is claimed is:

1. A wound dressing comprising a skin contact layer of apertured non-woven fabric, a liquid permeable top-sheet with a fluffed cellulose and superabsorbent polymer matrix, a silicone based skin heath treatment additive applied to the skin contact layer; a biocompatible foam cushion layer; and a liquid impermeable film comprising a vapor permeable back-sheet.

2. The wound dressing of claim 1, wherein the skin health treatment additive comprises an amount of lipids, triglycerides and vitamins in a triglyceride wax carrier.

3. The wound dressing of claim 1, wherein the skin health treatment additive is applied in a consistent manner to a geometric fabric shape selected from a square, a rectangle, a circle, a triangle, an oval, or combinations thereof.

4. The wound dressing of claim 1, wherein the biocompatible foam comprises polyurethane.

5. The wound dressing of claim 1, wherein the absorbent structure is conformable to the anatomical shape of the body of a human.

6. The wound dressing of claim 3, wherein the preferred geometric shape of the dressing is an oval or a rectangle.

7. A wound dressing comprising a permeable non-woven skin contact layer, a super-absorbent layer comprising superabsorbent particles fiberized into a fluffed cellulose matrix, a biocompatible foam layer, and a skin health treatment additive; wherein the skin health treatment additive is applied consistently and uniformly to the skin contact layer.

8. The wound dressing of claim 7, wherein the skin health treatment additive comprises a silicone based triglyceride wax carrier.

9. The wound dressing of claim 7, wherein the skin health treatment additive is applied in a geometric shape selected from a square, a rectangle, a circle, a triangle, an oval, or combinations thereof.

10. The wound dressing of claim 7, wherein the skin health treatment additive further comprises topical antibiotics, topical antimicrobials, bioengineered tissue regeneration drugs or combinations thereof.

11. The wound dressing of claim 1, wherein the skin contact layer has a geometric shape selected from the group consisting of a square, a rectangle, a circle, a triangle, an oval, or combinations thereof.

12. The wound dressing of claim 11, wherein the dressing has a geometric shape selected from the group consisting of an oval and a rectangle.

13. The wound dressing of claim 7, wherein the skin contact layer has a geometric shape selected from the group consisting of a square, a rectangle, a circle, a triangle, an oval, or combinations thereof.

14. The wound dressing of claim 13, wherein the dressing has a geometric shape selected from the group consisting of an oval and a rectangle.

* * * * *